US008937047B2

(12) United States Patent
Marino et al.

(10) Patent No.: US 8,937,047 B2
(45) Date of Patent: Jan. 20, 2015

(54) BIOKINETICS OF FAST-CLEARING POLYPEPTIDES (75) Inventors: Michael Ernest Marino, Clifton Park, NY (US); Faisal Ahmed Syud, Clifton Park, NY (US); Jason William Castle, Esperence, NY (US); Brian Duh-Lan Lee, Rexford, NY (US); Malin Lindborg, Hagersten (SE); Elin Gunneriusson, Saltsjobaden (SE); Christofer Lendel, Farsta (SE)

(73) Assignee: General Electric Company, Niskayuna, NY (US)

( * ) Notice: Subject to any disclaimer, the term of this patent is extended or adjusted under 35 U.S.C. 154(b) by 1128 days.

(21) Appl. No.: 12/002,972

(22) Filed: Dec. 19, 2007

(65) Prior Publication Data
US 2009/0180954 A1    Jul. 16, 2009

(51) Int. Cl.
*A61K 38/16* (2006.01)
*A61K 51/08* (2006.01)
*A61K 38/00* (2006.01)
*C07K 14/00* (2006.01)
*A61K 51/10* (2006.01)
*C07K 16/00* (2006.01)
*C07K 16/24* (2006.01)
*C07K 16/32* (2006.01)
*C07K 16/28* (2006.01)

(52) U.S. Cl.
CPC ......... *C07K 16/2863* (2013.01); *A61K 51/1084* (2013.01); *A61K 51/109* (2013.01); *C07K 16/00* (2013.01); *C07K 16/241* (2013.01); *C07K 16/32* (2013.01); *C07K 2318/20* (2013.01); *C07K 2319/00* (2013.01)
USPC .......................... 514/21.3; 424/1.69; 530/324

(58) Field of Classification Search
CPC ............ A61K 38/00; C07K 5/00; C07K 7/00; C07K 16/00; C07K 17/00
See application file for complete search history.

(56) References Cited

U.S. PATENT DOCUMENTS

| | | | |
|---|---|---|---|
| 5,322,678 | A | 6/1994 | Morgan, Jr. et al. |
| 6,020,163 | A | 2/2000 | Conklin |
| 6,673,559 | B1 | 1/2004 | Tsarfaty et al. |
| 7,118,915 | B2 | 10/2006 | Vogt et al. |
| 7,250,297 | B1 | 7/2007 | Beste et al. |
| 8,124,725 | B2 * | 2/2012 | Marino et al. ............... 530/324 |
| 2002/0052488 | A1 | 5/2002 | Boone et al. |
| 2006/0177831 | A1 | 8/2006 | Stemmer et al. |
| 2009/0180954 | A1 * | 7/2009 | Marino et al. ............... 424/1.69 |
| 2009/0191124 | A1 * | 7/2009 | Marino et al. ............... 424/1.69 |

FOREIGN PATENT DOCUMENTS

| | | |
|---|---|---|
| EP | 0329185 | 4/1994 |
| JP | 0228200 A | 1/1990 |
| WO | 2009041062 | 4/2009 |
| WO | 2009041643 | 4/2009 |

OTHER PUBLICATIONS

PCT Search Report, PCT/EP2008/067774, Mar. 6, 2009.
J. M. Jeong et al.,"Application of High Affinity Binding Concept to Radiolabel Avidin with Tc-99m Labeled biotin and the Effect of pI on Biodistribution," Nuclear Medicine and Biology, Elsevier Science Ltd., vol. 21, No. 7, 1994, pp. 935-940.
S. F. Rosebrough et al., Biochemical Modification of Streptavidin and Avidin: In Vitro and In Vivo Analysis, The Journal of Nuclear Medicine, vol. 37, No. 8, Aug. 1996, pp. 1380-1384.
F.J. Burczynski et al., "Hepatocyte [3H]-palmitate uptake: effect of albumin surface charge modification," Canadian Journal of Physiology and Pharmacology, NRC Research Press, ISSN: 008-4212, Oct. 1, 2001, pp. 868-875.
WO2009041062 Abstract, Apr. 2, 2009.
WO2009041643 Abstract, Apr. 2, 2009.
Skerra, Arne, "Lipocalins as a Scaffold", Biochimica et Biophysics Acta 1482, (2000), 337-350.
Mercader et al., "Generation of Anticalins with Specificity for a Nonsymmetric Phthalic Acid Ester", Analytical Biochemistry 308, (2002) 269-277.
Korndorfer et al, "Structural Mechanism of Secific Ligand Recognition by a Lipocalin Tailored for the Complexation of Digoxigenin", J. Mol. Biol. (2003) 330, pp. 385-396.
Korndorfer et al., "Crystallographic Analysis of an "Anticalin" With Tailored Specificity fpr Fluorescein Reveals High Structural Plasticity of the Lipocalin Loop Region", PROTEINS:Structure, Function, and Bioinformatics 53:121-129 (2003).
E. Bergsten et al., "PDGF-D is a specific, protease-activated ligand for the PDGF β-receptor," Nature Cell Biology, vol. 3, May 2001, pp. 512-516.
Unofficial English translation of Office Action from JP dated Sep. 17, 2013.

* cited by examiner

*Primary Examiner* — Maury Audet
(74) *Attorney, Agent, or Firm* — Jenifer E. Haeckl (57) ABSTRACT

Provided herein are methods of reducing liver uptake in vivo of a polypeptide that specifically binds to a target comprising: (a) providing a polypeptide that specifically binds to a target; and (b) substituting at least one basic or at least one neutral amino acid residue of the native polypeptide from step (a) with an acidic amino acid residue to produce a modified polypeptide, wherein the modified polypeptide demonstrates an isoelectric point at least 0.05-0.1 pH points less than the isoelectric point of the native polypeptide. Also provided are polypeptides made using the inventive methods as well as imaging techniques that employ the methods and agents.

4 Claims, 7 Drawing Sheets

BIOKINETICS OF FAST-CLEARING POLYPEPTIDES

FIELD

In general the field of invention relates to polypeptides that are capable of binding to a target. More specifically, the field of invention relates to low molecular weight binders that demonstrate favorable biokinetics and imaging methods using such fast clearing binders.

BACKGROUND

Specific binding of a target in a sample may be accomplished using a variety of binders, for example antibodies, affibodies, anticalins, aptamers. High molecular weight binders such as antibodies are disfavored for some in vivo applications (e.g., for imaging applications) because they take a long time to migrate to the target site, demonstrate poor tissue penetration, remain in the subject for a long time, are primarily cleared through the liver and are more likely to produce an immune response than smaller binders. Accordingly, for some in vivo applications low molecular weight, fast-clearing binders are preferred for rapid migration to a target site, tissue penetration, and rapid clearance from the body.

One fast-clearing binder is the Affibody, a 7 KDa polypeptide based on the z-domain of protein A. Affibodies all share a common three-helix protein fold. Affibodies against novel targets are generated by randomizing the 13 amino acid residues in the IgG-binding surface using phage or yeast display techniques. Affinity-matured proteins are produced as either a single 7 KDa domain (monovalent Affibody) or as two tandem 7 KDa domains (bivalent Affibody).

Fast-clearing binders that are particularly well suited for some in vivo applications because of their tissue penetration and low antigenicity, may nonetheless clear a body in a way that interferes with desired applications. For example, clearance via the liver could interfere with liver-based imaging applications; clearance via the kidney of a radiolabeled binder might result in unacceptable radiation dose to the kidneys; or fast clearance from the blood may need to be slowed to achieve penetration of difficult-to-access tissues.

Accordingly, needs exist for methods to modify biokinetics of fast-clearing binders. Moreover, needs exist for fast-clearing biokinetically tuned binders for in vivo imaging that may be used for a variety of imaging modalities for preclinical or diagnostic imaging.

BRIEF DESCRIPTION

Provided herein are methods of reducing liver uptake of a fast-clearing polypeptide that specifically binds to a target comprising: providing a polypeptide that specifically binds to a target; and substituting at least one basic or at least one neutral amino acid residue with an acidic amino acid residue to produce a modified polypeptide, wherein the modified polypeptide demonstrates an isoelectric point at least 0.05-0.1 pH points less than the isoelectric point of the native polypeptide.

In some embodiments, the blood ½ life of the modified polypeptide is substantially the same as the blood ½ life of the native polypeptide and the liver uptake of the modified polypeptide is substantially reduced relative to the native polypeptide.

In some embodiments, the polypeptide consists essentially of about 60 amino acid residues comprising an alpha helical fold or about 120 amino acid residues comprising a pair of alpha helical fold segments. Alternatively, the polypeptide may consist essentially of about 160 amino acid residues comprising a beta-barrel type fold.

In all embodiments, the modified polypeptide retains binding affinity for its native target and, thus, binds the target with at least 50%, 75%, 90% specificity of the unmodified polypeptide.

In some embodiments, the basic amino acid residues are selected from histidine, lysine, and arginine and the acidic amino acid residues are selected from aspartic acid or glutamic acid. And, the neutral amino acid residues may be selected from any amino acid residue other than histidine, lysine, arginine, aspartic acid, or glutamic acid and the acidic amino acid residues are selected from aspartic acid or glutamic acid, and derivatives thereof.

A signal generator such as radioactive, fluorescent, magnetic, radioopaque (e.g., Tc99m or F18), luminescent, phosphorescent, isotopic, or ultrasound opaque signal generator may be appended to the modified polypeptide. Optionally or additionally, a targeting moiety is appended to the modified polypeptide.

Also provided herein are polypeptides made according to the disclosed methods, including isolated polypeptide consisting essentially of the amino acid amino acid residues of SEQ ID NOS. 1-9.

Also provided herein are methods of reducing background noise in the liver during an imaging procedure using a fast-clearing polypeptide, comprising:

(a) providing a polypeptide that specifically binds to a target; and (b) substituting at least one basic or at least one neutral amino acid residue with an acidic amino acid residue to produce a modified polypeptide, wherein the modified polypeptide demonstrates an isoelectric point at least 0.05-0.1 pH points less than the isoelectric point of the native polypeptide;

(c) introducing the modified polypeptide into a subject as part of an imaging procedure; and (d) imaging the subject with a modality appropriate for detecting the modified polypeptide.

FIGURES

These and other features, aspects, and advantages of the present invention will become better understood when the following detailed description is read with reference to the accompanying figures.

FIG. 2 shows kidney and liver clearance for 5 monomeric affibodies. The percent of the total injected quantity of affibody remaining in each gram of tissue is shown for liver (panel 2A) and kidney (panel 2B) plotted against the time elapsed after injection. The data demonstrate a broad range of retention values, showing that the sequence variability within the panel of affibodies is sufficient to direct them to the liver or kidneys for clearance.

FIG. 5 shows blood clearance for 2 dimeric affibodies. The percent of the total injected quantity of affibody remaining in the blood (in circulation) is shown on the y-axis. The time post-injection is shown on the x-axis. The data demonstrates that despite sequence variation, the affibodies exhibit similar clearance characteristics.

FIG. 6 shows kidney and liver clearance for dimeric affibodies. The percent of the total injected quantity of affibody remaining in each gram of tissue is shown for liver (left) and kidney (right) plotted against the time elapsed after injection. The data demonstrate a broad range of retention values, showing that the sequence variability within the panel of affibodies is sufficient to direct them to the liver or kidneys for clearance.

DETAILED DESCRIPTION

The following detailed description is exemplary and not intended to limit the invention of the application and uses of the invention. Furthermore, there is no intention to be limited by any theory presented in the preceding background of the invention of the following detailed description.

To more clearly and concisely describe and point out the subject matter of the claimed invention, the following definitions are provided for specific terms that are used in the following description and the claims appended hereto.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, γ-carboxyglutamate, O-phosphoserine, phosphothreonine, and phosphotyrosine. Categories of amino acids herein defined are not mutually exclusive. Thus, amino acids having side chains exhibiting two or more physical-chemical properties may be included in multiple categories. For example, amino acid side chains having aromatic moieties that are further substituted with polar substituents, such as Tyr (Y), may exhibit both aromatic hydrophobic properties and polar or hydrophilic properties, and may therefore be included in both the aromatic and polar categories. The appropriate categorization of any amino acid will be apparent to those of skill in the art, in light of the detailed disclosure provided herein.

"Basic Amino Acid" refers to a hydrophilic amino acid having a side chain pK value of greater than 7. Basic amino acids typically have positively charged side chains at physiological pH due to association with hydronium ion. Genetically encoded basic amino acids include H is (H), Arg (R), and Lys (K).

"Binding target" refers to any agent that may be bound by a binder. A binding target may include one or more of peptides, proteins (e.g., antibodies), nucleic acids (e.g., polynucleotides, DNA, RNA, or aptamers); polysaccharides (e.g., lectins or sugars), lipids, enzymes, enzyme substrates, ligands, receptors, antigens, or haptens. The target may include a discrete chemical moiety or a three-dimensional structural component (e.g., 3D structures that arises from peptide folding).

"Binding" refers to the ability of a binder to preferentially bind to target with an affinity that is at least two-fold greater than its affinity for binding to a non-specific target (e.g., BSA or casein) other than the predetermined target or a closely-related target. The binders provided herein bind their respective targets with an affinity with a KD value less than about $1 \times 10^6$ M$^{-1}$, more preferably less than about $1 \times 10^7$ M$^{-1}$, and most preferably less than about $1 \times 10^8$ M$^{-1}$. Similarly, "specific binding" refers to the property of a binder to bind to a predetermined antigen with an affinity with a KD value less than about $1 \times 10^7$ M$^{-1}$.

As used herein, the phrase "blood half-life" refers to the time required for the plasma concentration of an agent to decline by one-half when elimination is first-order or pseudo-first order. In the case of multiple decay phases, the term "blood half life" refers to either the apparent half-life (if the decay half-lives for different phases are similar) or the dominant half-life (that accounting for the bulk of the clearance) if the different half-lives are dissimilar.

As used herein, the term "fluorophore" refers to a chemical compound, which when excited by exposure to a particular wavelength of light, emits light (at a different wavelength. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example Texas Red, Cy5, and tetramethylrhodamine) may be characterized by their emission at wavelengths generally in the range of 590-690 nanometers. Examples of fluorophores include, but are not limited to, 4-acetamido-4'-isothiocyanatostilbene-2,2'disulfonic acid, acridine, derivatives of acridine and acridine isothiocyanate, 5-(2'-aminoethyl)aminonaphthalene-1-sulfonic acid (EDANS), 4-amino-N-[3-vinylsulfonyl)phenyl] naphthalimide-3,5 disulfonate (Lucifer Yellow VS), N-(4-anilino-1-naphthyl)maleimide, anthranilamide, Brilliant Yellow, coumarin, coumarin derivatives, 7-amino-4-methyl-coumarin (AMC, Coumarin 120), 7-amino-trifluoromethyl-couluarin (Coumaran 151), cyanosine; 4',6-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin, -, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), eosin, derivatives of eosin such as eosin isothiocyanate, erythrosine, derivatives of erythrosine such as erythrosine B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein, fluorescein isothiocyanate (FITC), QFITC (XRITC); fluorescamine derivative (fluorescent upon reaction with amines); IR144; IR1446; Malachite Green isothiocyanate; 4-methylumbelliferone; ortho cresolphthalein; nitrotyrosine; pararosaniline; Phenol Red, B-phycoerythrin; o-phthaldialdehyde derivative (fluorescent upon reaction with amines); pyrene and derivatives such as pyrene, pyrene butyrate and succinimidyl 1-pyrene butyrate; Reactive Red 4 (Cibacron .RTM. Brilliant Red 3B-A), rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl Rhodamine, tetramethyl rhodamine isothiocyanate (TRITC); riboflavin; rosolic acid and lathanide chelate derivatives, quantum dots, cyanines, and squaraines.

As used herein, the term "isoelectric point" refers to the pH at which a molecule carries no net electrical charge. Isoelectric points can be determined experimentally, or can be calculated for polypeptides based on primary sequence.

As used herein the term "paramagnetic metal ion", "paramagnetic ion" or "metal ion" refers to a metal ion that is magnetized parallel or antiparallel to a magnetic field to an extent proportional to the field. Generally, these are metal ions that have unpaired electrons. Examples of suitable paramagnetic metal ions, include, but are not limited to, gadolinium III (Gd+3 or Gd(III)), iron III (Fe+3 or Fe(III)), manganese II (Mn+2 or Mn(II)), yttrium III (Yt+3 or Yt(III)), dysprosium (Dy+3 or Dy(III)), and chromium (Cr(III) or Cr+3). In some embodiments, the paramagnetic ion is the lanthanide atom Gd(III), due to its high magnetic moment (u 2=63BM2), a symmetric electronic ground state (S8), and its current approval for diagnostic use in mammals.

"Percentage of sequence identity" means the value determined by comparing two optimally aligned sequences over a comparison window, wherein the portion of the polynucleotide or polypeptide sequence in the comparison window may comprise additions, substitutions, or deletions (i.e., gaps) as compared to the reference sequence (which does not comprise additions, substitutions, or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "protein", "peptide" and "polypeptide" are used herein to describe any chain of amino acids, regardless of length or post-translational modification (for example, glycosylation or phosphorylation). Thus, the terms may be used interchangeably herein to refer to a polymer of amino acid residues. The terms also apply to amino acid polymers in which one or more amino acid residue is an artificial chemical mimetic of a corresponding naturally occurring amino acid. Thus, the term "polypeptide" includes full-length, naturally occurring proteins as well as recombinantly or synthetically produced polypeptides that correspond to a full-length naturally occurring protein or to particular domains or portions of a naturally occurring protein. The term also encompasses mature proteins, which have an added amino-terminal methionine to facilitate expression in prokaryotic cells. The polypeptides of the invention may be chemically synthesized or synthesized by recombinant DNA methods; or, they may be purified from tissues in which they are naturally expressed, according to standard biochemical methods of purification.

As used herein the term "physiological conditions" refers to conditions generally present in a mammalian body. Thus, physiological conditions mean a pH of about 6.5 to about 7.5 and temperature ranging from about 25° C. to about 37° C.

As used herein, the term "radionuclide" generally refers to any atom that can be traced by radioactive detection following introduction into a subject. Representative radioactive atoms include: fluorine-18, actinium-225, bismuth-212, arsenic-72, indium-110, indium-111, indium-113m, gallium-67, gallium-68, strontium-83, zirconium-89, ruthenium-95, ruthenium-97, ruthenium-103, ruthenium-105, mercury-107, mercury-203, rhenium-186, rhenium-188, tellurium-121 m, tellurium-122m, tellurium-125m, thulium-165, thulium-167, thulium-168, technetium-94m, technetium-99m, silver-111, platinum-197, palladium-109, copper-62, copper-64, copper-67, yttrium-86, yttrium-90, scandium-47, samarium-153, lutetium-177, rhodium-105, praseodymium-142, praseodymium-143, terbium-161, holmium-166, gold-199, cobalt-57, cobalt-58, chromium-51, iron-59, selenium-75, thallium-201, or ytterbium-169.

The term "anticalin scaffold" refers to those amino acid residues of the polypeptide that provide the three-dimensional structure of a cylindrical β-barrel comprised of eight antiparallel β-strands connected by one or more loops to adequately position one end of the barrel with target-binding loops such that binding to a target is enabled The term "affibody scaffold" with reference generally refers to those amino acid residues of the polypeptide that provide the three-dimensional structure to adequately position the binding interface amino acid residues of the polypeptide such that binding to a target is enabled. Any sequence that preserves the binding site and binding activity with the same topology (the z-domain three-helical fold) is based on the affibody scaffold.

The term "substantial identity" or "homologous" in their various grammatical forms in the context of peptides indicates that a peptide comprises a sequence that has a desired identity, for example, at least 80%, 85%, 90%, or 95% sequence identity to the reference sequence over a specified comparison window.

As used herein, the term "signal generator" refers to a molecule capable of providing a detectable signal using one or more detection techniques (e.g., spectrometry, calorimetry, spectroscopy, or visual inspection). Suitable examples of a detectable signal may include an optical signal, and electrical signal, or a radioactive signal. Examples of signal generators useful in the inventive methods include, for example, a chromophore, a fluorophore, a Raman-active tag, a radioactive label, an enzyme, an enzyme substrate, or combinations thereof. Suitable radioisotopes may include $^{3}$H, $^{11}$C, $^{14}$C, $^{18}$F, $^{32}$P, $^{35}$S, $^{123}$I, $^{125}$I, $^{131}$I, $^{51}$Cr, $^{36}$Cl, $^{57}$Co, $^{59}$Fe, $^{75}$Se, and $^{152}$Eu. Isotopes of halogens (such as chlorine, fluorine, bromine and iodine), and metals including technetium, yttrium, rhenium, and indium are also useful labels. Typical examples of metallic ions that may be used as signal generators include $^{99m}$Tc, $^{123}$I, $^{111}$In, $^{131}$I, $^{97}$Ru, $^{67}$Cu, $^{67}$Ga, $^{125}$I, $^{68}$Ga, $^{72}$As, $^{89}$Zr, and $^{201}$Tl. Radioisotopes for in vivo diagnostic imaging by positron emission tomography ("PET") include $^{11}$C, $^{18}$F, and $^{123}$I. Paramagnetic labels may be metal ions are present in the form of metal complexes or metal oxide particles. Suitable paramagnetic isotopes may include $^{157}$Gd, $^{55}$Mn, $^{162}$Dy, $^{52}$Cr, and $^{56}$Fe.

As used herein, the term "targeting moiety" refers to a chemical species (i.e., an organic molecule or a biomolecule) that recognizes and specifically binds to one or more proteins in a protein-protein complex. In some embodiments, the target moiety is capable of binding to protein fragments near or adjacent to the portions that transiently interact (e.g., interact only for seconds or minutes).

Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Embodiments

Provided herein are methods for tuning biokinetics of a protein sequence by altering the isoelectric point, to the increase or decrease in vivo liver and/or kidney metabolism. Also provided are polypeptides that have been altered using the present methods to demonstrate tuned biokinetics. Further provided are in vivo imaging methods (e.g., preclinical imaging or diagnostic imaging using the polypeptides provided herein.

In general, the methods provided herein enable one of ordinary skill in the art to tuning the biokinetics of a polypeptide by altering the isoelectric point of the polypeptide. Methods available for substitution of amino acids include mutagenesis of the cDNA encoding the described polypeptide by a number of methods known to those skilled in the art, including random mutagenesis, site-directed mutagenesis, and mutagenesis using error prone PCR. One method to introduce random substitutions into the binding interface positions is the use of DNA containing degenerate primers at the codons of desired substitution. Alternatively, the polypeptides may be generated using standard synthetic peptide synthesis techniques.

Table 1 (below) provides general guidelines for substitution types in various types of fast-clearing binders. The shift column indicates which direction the isoelectric point will shift for the corresponding type of substitution.

TABLE 1

| Original | Substitution | Shift | Impact |
|----------|--------------|----------|--------|
| Basic | Acidic | Negative | High |
| Neutral | Acidic | Negative | Medium |
| Acidic | Basic | Positive | High |
| Neutral | Basic | Positive | Medium |

Table 2 below provides pH characterizations of representative amino acids.

TABLE 2

| Amino Acid | Charge |
|------------|--------|
| Alanine (A) | Neutral |
| Phenylalanine (F) | Neutral |
| Glycine (G) | Neutral |
| Isoleucine (I) | Neutral |
| Leucine (L) | Neutral |
| Methionine (M) | Neutral |
| Asparagine (N) | Neutral |
| Proline (P) | Neutral |
| Glutamine (Q) | Neutral |
| Serine (S) | Neutral |
| Selenocysteine (U) | Neutral |
| Valine (V) | Neutral |
| Tryptophan (W) | Neutral |
| Tyrosine (Y) | Neutral |
| Cysteine (C) | Acidic |
| Aspartic acid (D) | Acidic |
| Glutamic acid (E) | Acidic |
| Lysine (K) | Basic |
| Arginine (R) | Basic |
| Threonine | Weak acidic |
| Histidine | Weak basic |

Although, the scaffold portions of the polypeptides are preferred to be unchanged so as to preserve tertiary structure, conservative and non-conservative mutations in scaffold amino acid residues that do not result in a loss of binding are permitted.

The polypeptide sequences referred to herein are listed in Table 3 below. The polypeptides identified as SEQ. ID. NO.: 1-8.

TABLE 3

| SEQ. ID. NO.: | Sequence | Identifier | Residues | Target |
|---------------|----------|------------|----------|--------|
| SEQ. ID. NO.: 1 | GSSHHHHHHLQVDN KFNKERQVAAAEIDA LPNLNRGQWNAFIAS LVDDPSQSANLLAEA KKLNDAQAPKVD | Z1977 | 71 | PDGF-Rβ |
| SEQ. ID. NO.: 2 | GSSHHHHHHLQVDN KFNKELSDAAQEIDSL PNLNRSQWNAFIKSLI DDPSQSANLLAEAKK LNDAQAPKVD | Z1978 | 71 | PDGF-Rβ |
| SEQ. ID. NO.: 3 | GSSHHHHHHLQVDN KFNKERREAAKEIDSL PNLNRTQWNAFIRSL ADDPSQSANLLAEAK KLNDAQAPKVD | Z1980 | 71 | PDGF-Rβ |
| SEQ. ID. NO.: 4 | GSSHHHHHHLQVDN KFNKELVRAAQEIDEL PNLN RGQWNAFIKSL VDDPSQSANLLAEAK KLNDAQAPKVD | Z1982 | 71 | PDGF-Rβ |

TABLE 3-continued

| SEQ. ID. NO.: | Sequence | Identifier | Residues | Target |
|---|---|---|---|---|
| SEQ. ID. NO.: 5 | GSSHHHHHHLQVDN KFNKERLKAAAEIDAL PNLNRKQWNAFISSL RDDPSQSANLLAEAK KLNDAQAPKVD | Z1995 | 71 | PDGF-Rβ |
| SEQ. ID. NO.: 6 | GSHHHHHHLQVDNK FNKELIEAAAEIDALP NLNRRQWNAFIKSLV DDPSQSANLLAEAKK LNDAQAPKVDC | Z2465 | 71 | PDGF-Rβ |
| SEQ. ID. NO.: 7 | GSHHHHHHLQVDNK FNKELIAAAAEIDRLP NLNRVQWNAFIKSLV DDPSQSANLLAEAKK LNDAQAPKVDC | Z2477 | 71 | PDGF-Rβ |
| SEQ. ID. NO.: 8 | GSHHHHHHLQVDNK FNKELVKAAAEIDALP NLNRRQWNAFIKSLV DDPSQSANLLAEAKK LNDAQAPKVDC | Z2483 | 71 | PDGF-Rβ |

Performance Characteristics

Figure 1:
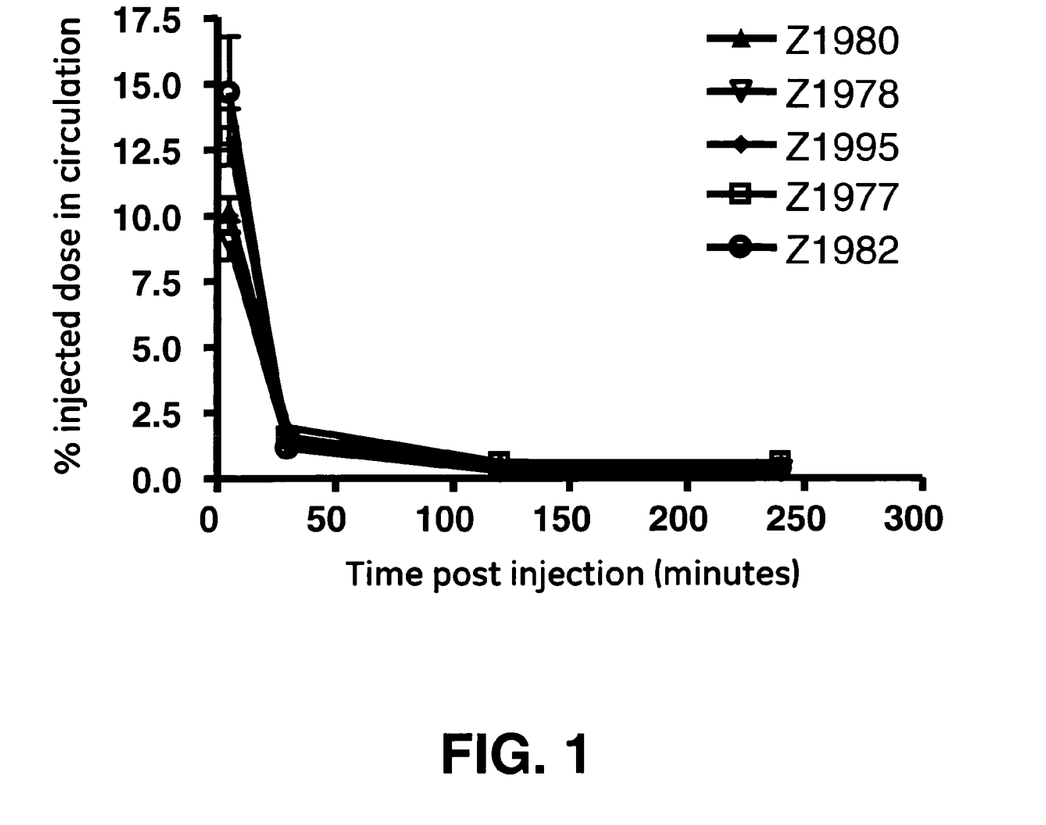
FIG. 1 shows the blood clearance for 5 monomeric affibodies that have been modified in accordance with the teachings herein. The percent of the total injected quantity of affibody remaining in the blood (in circulation) is shown on the y-axis. The time post-injection is shown on the x-axis. The data demonstrates that despite sequence variation, the affibodies exhibit similar clearance characteristics.

Table 4 provides the results of analysis of blood clearance for monomeric affibodies, corresponding to the plot shown in FIG. 1, which demonstrates quantitatively that five unmodified affibodies exhibit similar blood behavior despite sequence variation.

TABLE 4

| Affibody | $t_{1/2}$ (min) | AUC (0-120) | $R^2$ ($t_{1/2}$ fit) |
|---|---|---|---|
| Z1980 | 1.4570 | 542.7 | 0.9998 |
| Z1978 | 1.4040 | 476.3 | 0.9997 |
| Z1995 | 1.4620 | 495.5 | 0.9998 |
| Z1977 | 1.6460 | 560.9 | 0.9996 |
| Z1982 | 1.7720 | 548.3 | 0.9987 |

Figure 5:
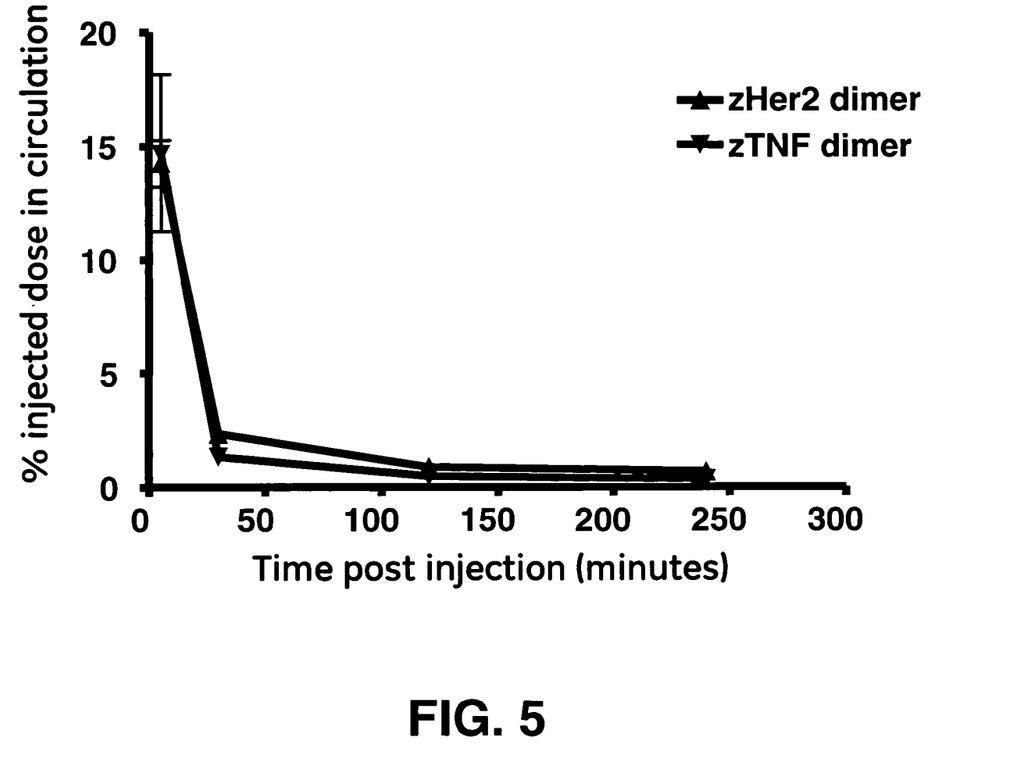

Table 5 provides the results of an analysis of blood clearance for bivalent affibodies, corresponding to the plot shown in FIG. 5, which demonstrates quantitatively that the two bivalent affibodies exhibit similar blood behavior despite sequence variation.

TABLE 5

| Affibody | $t_{1/2}$ (min) | AUC (0-120) | $R^2$ ($t_{1/2}$ fit) |
|---|---|---|---|
| zHer2 | 1.706 | 725 | 0.9995 |
| ZTNF | 1.767 | 618 | 0.9968 |

In general, the fast-clearing binders provided herein may be used to perform the functions that other binders (e.g., antibodies) are used to perform. Thus, the fast-clearing binders may be used, for example, as imaging agents for in vivo diagnosis. When used in vivo, the fast-clearing binders may be modified with an appropriate signal generator (e.g., 18F for PET imaging or 99 mTc for SPECT imaging) for the imaging modality chosen.

The disclosed methods provide various advantages over other methods for controlling clearance and metabolism. Typical post-translational modification (e.g., pegylation or glycosylation) relies on chemical modifications made to a protein after its production. Post-translation modification may cause proteins to aggregate or unfold, and hence lose activity. Additionally, post-translational modifications frequently produce heterogeneous mixtures of proteins, a feature that is undesirable for injectable formulations. The essentially homogeneous mixtures of proteins produced using the methods disclosed herein may be introduced into a subject with out the additional time-consuming and expensive enrichment steps that are required for heterogeneous protein mixtures produced using post-translational modification techniques.

Additional sequence may be added to the termini to impart selected functionality. Thus, additional sequences may be appended to one or both termini to facilitate purification or isolation of a binder, alone or coupled to a binding target (e.g., by appending a his tag to the polypeptide). A signal generator may be incorporated into the polypeptide at terminal position or at an internal position. Suitable examples of signal generators may include a chromophore, a fluorophore, a Raman-active tag, a radioactive label, an enzyme, an enzyme substrate, or combinations thereof. Suitable examples of a detectable signal may include an optical signal, and electrical signal, or a radioactive signal.

To assess the target levels, a labeled imaging agent is delivered to a subject. Typically, the subject is a mammal and can be human. The labeled imaging agent is delivered to a subject by a medically appropriate means. After allowing a clearance time according to the label chosen, the amount of imaging agent bound to target is determined by measuring the emitted signal using an imaging modality. The visual and quantitative analyses of the resulting images provide an accurate assessment of the global and local levels of target in the subject.

The present disclosure relates to a method of non-invasively assessing levels of target to diagnose diseases associated with a particular biomarker, for example imaging cancer with c-met or imaging liver and cardiovascular disease with PDGF-RB. The disclosed biokinetic tuning methods enhance qualitatively and quantitatively determine target levels in vivo and may be used to determine the efficacy of related therapies used particular diseases.

The compositions of this invention can be administered to humans and other animals parenterally. The term "parenteral" administration as used herein refers to modes of administration including intravenous, intramuscular, intraperitoneal, intrasternal, subcutaneous and intraarticular injection and infusion. Pharmaceutical compositions of this invention for parenteral injection comprise pharmaceutically-acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents, which delay absorption such as aluminum monostearate and gelatin.

EXAMPLES

Practice of the invention will be still more fully understood from the following examples, which are presented herein for illustration only and should not be construed as limiting the invention in any way. The invention provides a method by which the rapid clearance of binders from the blood can be directed to different organs by changing protein sequence to effect a change in isoelectric point. The examples below demonstrate four different situations wherein the isoelectric point of polypeptide binders was varied and shown to drive the blood clearance to the desired organ.

Materials and Methods

For the following experiments, three types of proteins were used: a 7 KDa monovalent Affibody, a 14 KDa bivalent Affibody. All three proteins are engineered proteins with affinities to specific targets. Multiple sets of affibodies with very similar secondary and tertiary protein structure, but different sequences, were used for the current studies. The proteins were produced recombinantly and purified. Eight 7 kDa affibodies of varying sequence, two 14 KDa affibodies of varying sequence of varying sequence were used.

Sequence variations Protein sequences described herein were varied using phage display (e.g., as reported by G. P. Smith in "Filamentous Fusion Phage: Novel Expression Vectors That Display Cloned Antigens on the Virion Surface", Science, 228, Pp 1315-1317, 1985). Recombinantly produced affibody sequences may be varied using a variety of other techniques as well, including site directed mutagenesis, degenerate PCR, multi-site mutagenesis, truncation, and other microbiological techniques for generating mutants, variants, or substitutions of an existing protein. The nature of the substitutions made would be dependent on the desired change in protein properties. Proteins may also be produced synthetically (e.g., on a peptide synthesizer), and a variety of chemical techniques for substituting amino acids (e.g., direct incorporation of substituted or modified amino acids during synthesis) are appropriate for this scenario. Amino acids that are not naturally occurring, if desired, are most easily substituted into a protein when it is produced on a synthesizer.

Residue Selection Most amino acids on the Affibody scaffold may be varied. 14 amino acid positions in the Affibody are frequently varied and have no impact on the structure of affibodies when varied. These amino acid residues were varied for the studies described here, using the techniques described above. Surface-exposed amino acid residues (partially or completely solvent exposed) of proteins may also often be varied without any meaningful impact on the secondary or tertiary structure of a protein (in the case of a binder, such substitutions often have no impact on its ability to bind its target). The surface amino acid residues of affibodies are known and are also possible targets for sequence variation. The hydrophobic core of the proteins is also known, and is an unlikely target for variation, although some examples exist where core amino acid residues of a protein are varied without impacting the structure or function of a protein. Residue choice may be further based on the desired change in properties of the parent molecule. Table 1 classifies general types of substitutions and their effects of the isoelectric point.

Chelators and Bioconjugation In some cases, proteins were produced with a "6-his" tag that was used for direct conjugation of radiometals as described below. In other cases, a chelator for radiometals was conjugated to proteins after their production. The hynic chelator for 99 mTc was conjugated to proteins using either NHS chemistry to link it covalently to primary amines in the protein, or maleimide chemistry to link it covalently to free cysteines. The techniques for this approach are described in the literature, and a number of vendors sell kits or reagents for this type of post-translational modification with chelators. Other techniques for conjugating chelators to proteins or functionalizing proteins would also be applicable in this case.

Labeling via the 6-his tag. Labeling of proteins with the fac-[99 mTc(CO)3]+ core was accomplished using modifications to a previously published procedure (as described in Waibel, R.; Alberto, R.; Willuda, J.; Finnern, R.; Schibli, R.; Stichelberger, A.; Egli, A.; Abram, U.; Mach, J.-P.; Plückthun, A.; Schubiger, P. A. Nat. Biotechnol. 1999, 17, 897.). Briefly, Na[$^{99m}$TcO$_4$] in saline (4 mCi, 2 mL) was added to an Isolink® boranocarbonate kit (gifted by Mallinckrodt, see reference; Alberto, R.; Ortner, K.; Wheatley, N.; Schibli, R.; Schubiger, A. P. J. Am. Chem. Soc. 2001, 123, 3135.). The resulting solution was heated to 95° C. for 15-20 minutes, to give fac-[$^{99m}$Tc(CO)$_3$(H$_2$O)$_3$]$^+$. A portion (2 mCi, 1 mL) of the solution was removed and neutralized to pH ~7 with 1 N HCl. A 325-µL aliquot was removed and added to a solution of the His$_6$-protein. The resulting solution was heated in a water bath at 35-37° C. for 40 minutes. Typical radiochemical yields ranged from 80-95% (determined by ITLC-SG, Biodex, 0.9% NaCl). The crude reaction products were chromatographed on a NAP-5 column (GE Healthcare, 10 mM PBS) to give products of >99% radiochemical purity. Typical specific activities obtained were 3-4 µCi/µg. The resulting solution was then diluted with 10 mM PBS to give the proper concentration for subsequent biodistribution studies.

Labeling via the hynic chelator: The synthesis of 99 mTc (tricine)$_2$(HYNIC-Affi) was accomplished according to published methods. Briefly, 200 µL of a 10 mM PBS solution of tricine (Fluka; 90 mg/mL), 100 µL of a solution of stannous chloride dihydrate (Sigma-Aldrich; 250 µg/mL in 0.1 N HCl), and 60 µL of 0.1 N NaOH were combined to give a solution of pH 6-7. To this was added 200 µL of Na[99 mTcO4] in saline (Cardinal Health; 2 mCi/mL). After 15 minutes at RT, the solution was checked for 99 mTc-colloid by ITLC (Biodex; 0.9% NaCl). Colloid was always <5%. For 14 KDa HYNIC-Affibodies, 20 µL (30 µg) were added to the resulting 99mTc-tricine solution. This solution was incubated at RT for 25 minutes. For 7 KDa HYNIC-Affibodies, 100 μCi of 99mTc-tricine were removed and added to solution of 17 μg of HYNIC-protein. This solution was incubated at RT for 25 minutes. NAP-5 purification was carried out to remove the unreacted starting materials, giving the desired compound in >99% radiochemical purity at a specific activity of μCi/μg (21 Ci/mmol). HPLC (Grace-Vydac Peptide/Protein C4 column) was performed on the purified radiolabeled species.

Animals and Animal Models: Biodistribution studies were carried out in normal female C57/B16 mice (Charles River Labs, Hopkinton, Mass.) with an age range between 8 and 15 weeks. Mice were housed for at least 48 hours before biodistribution experiments were carried out. Some additional biodistribution experiments were carried out in naïve or tumor-bearing CD-1 nude mice from the same vendor and the same age range and sex. Statistical comparisons of biodistribution data from the different mouse types indicate that strain and tumor status does not influence biodistribution parameters ($p<0.05$) in all organs compared (the major clearance organs—blood, liver, kidney, bladder/urine).

Biodistribution: Mice were given tail-vein injections of ~1 ug of 99 mTc-labeled protein (~3 uCi/1 ug). Mice were placed in filter-paper lined cages until euthanasia. Three mice were euthanized at each time point (5, 30, 120, and 240 minutes) and tissues of interest dissected and counted on a Perkin Elmer 1480 Gamma Counter. Data were collected for blood, kidney, liver, spleen, and injection site (tail). Urine from cages was pooled with the bladder and also counted. The remaining tissues were counted and the sum of all tissues plus urine for each animal was summed to provide the total injected dose. The %-injected dose for each organ was determined based on this total, and organs were weighed for determination of the %-injected dose per gram, (% ID/g). Data is reported as mean value for all three mice in the time point with error bars representing the standard deviation of the group.

Blood clearance parameters: half-life is determined by converting the % ID/g in blood to a % ID total in the bloodstream. The assumption is made that the % ID in the blood at time zero is 100%. The data is fit with a monoexponential curve using a least squares analysis (Prism, GraphPad Software, www.graphpad.com). The half-life, in minutes, is extracted as a fitted parameter. R-squared values are generally in excess of 0.97. The AUC is obtained by numerically integrating the curve generated above.

Determination of Isoelectric Point: Isoelectric points were calculated based on primary sequences (see Table 2) using the method described by Bjellqvist B, Hughes G J, Pasquali C, Paquet N, Ravier F, Sanchez J C, Frutiger S, and Hochstrasser D. in "The focusing positions of polypeptides in immobilized pH gradients can be predicted from their amino acid sequences." Electrophoresis. 1993 October; 14(10):1023-31.

Example 1

A Panel of Five Monomeric Affibodies

The goal of this study was to engineer an affibody with the low liver uptake. Five monomeric affibodies with a wide range of isoelectric points were chosen for this study. The range of isoelectric points, calculated as described above, was between 6.5 and 10.0. The affibodies are designated with their development codes, which are "Z1977", "Z1978", "Z1980", "Z1982", and "Z1995".

The affibodies were labeled via their 6-his tags (as described above). Radiochemical purity after purification was in excess of 99% for all five affibodies.

Biodistribution was carried out as described above. The five affibodies were observed to have similar blood clearance profiles (FIG. 1). The blood data was subjected to a least squares fit of a monoexponential decay curve in order to determine serum half-life. The resulting curves were integrated to generate area-under-curve (AUC) values. These data and analyses show that the overall in vivo behavior of affibodies is largely unchanged by the sequence variations (Table 3).

Figures 2A, 2B:
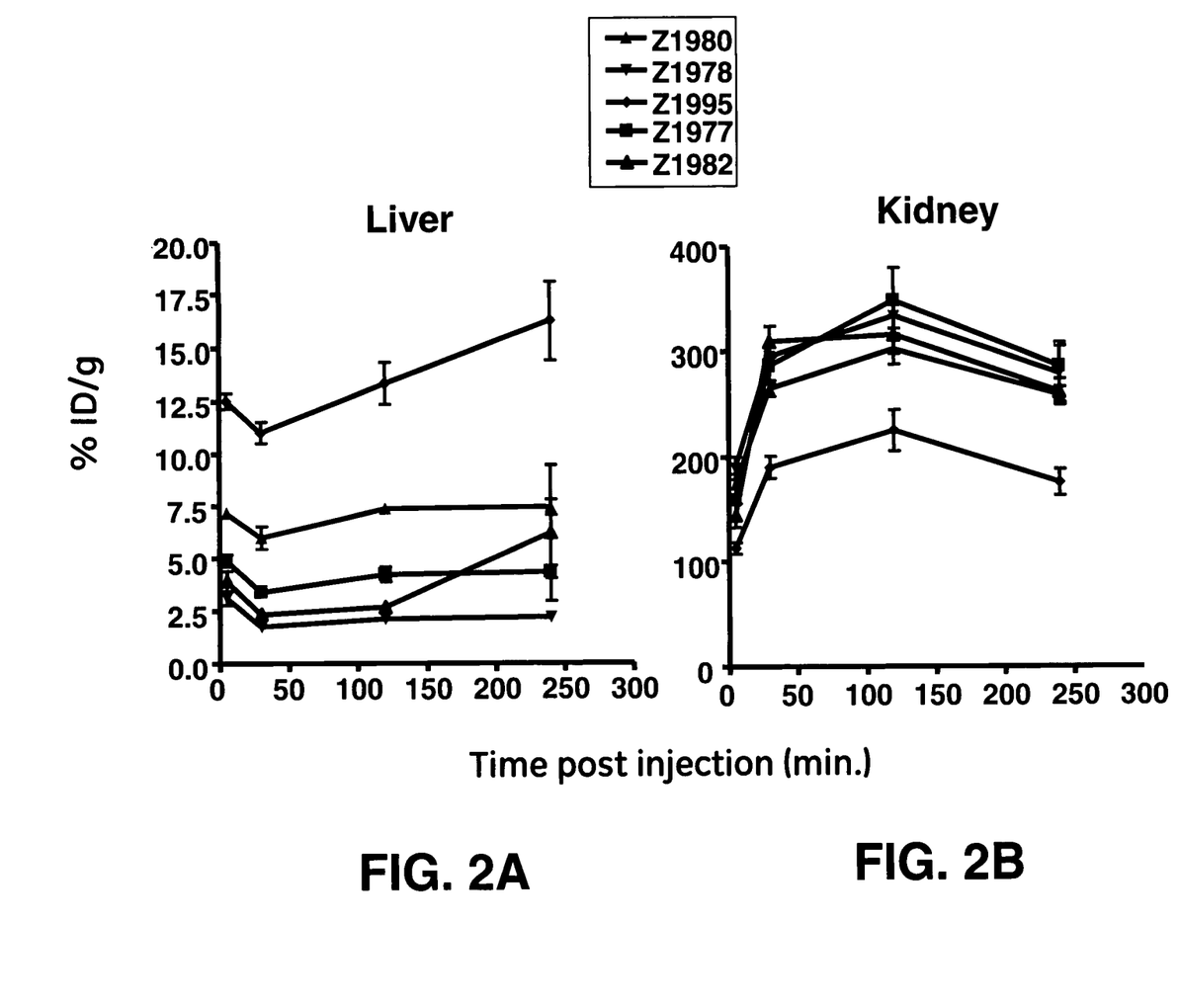
Figure 3:
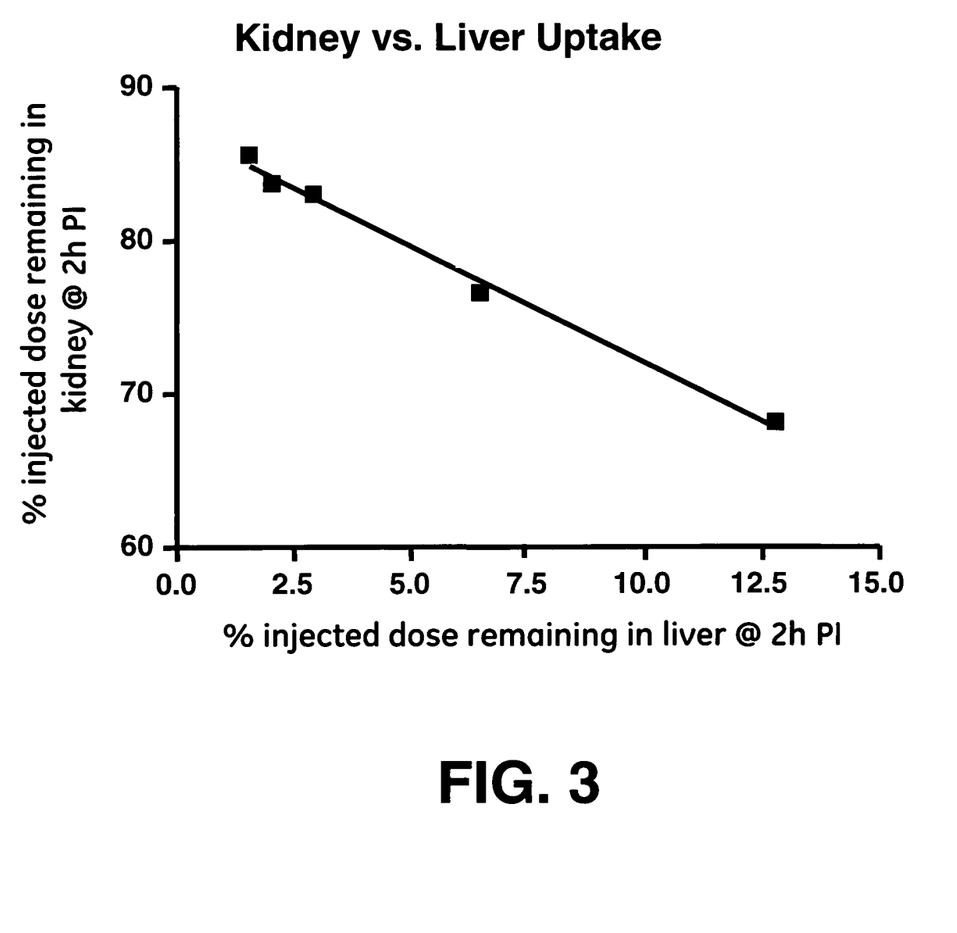
FIG. 3 shows the correlation of liver- and kidney-mediated clearance of affibodies. The two are inversely correlated, showing that the affibodies are removed from the bloodstream by both the liver and kidneys, and that the sequence variation in this panel of affibodies is sufficient to shift this clearance one way or the other.

While the blood clearance was very similar, the five affibodies were observed to have markedly different levels of liver and kidney retention (FIG. 2). The kidney and liver uptake values were found to be inversely correlated (FIG. 3). This data shows that the liver and the kidneys effect the removal of affibodies from the blood, and that while the clearance rate is the same, the distribution between the two is different. This difference is of key interest because the ability to drive the molecule away from the liver and into the kidneys or the reverse has value when developing affibodies for clinical purposes. This is especially valuable if it can be done without altering the other behaviors of the molecule.

The sequences of the affibodies were used to evaluate the magnitude of the impact of sequence on clearance mechanism. Table 2 shows the sequences of the affibodies that were used in the studies reported here. A small number of amino acid residues known not to impact the structure of the molecule were varied between the different affibodies. The sequences were analyzed to determine their isoelectric points as described above.

Figure 4:
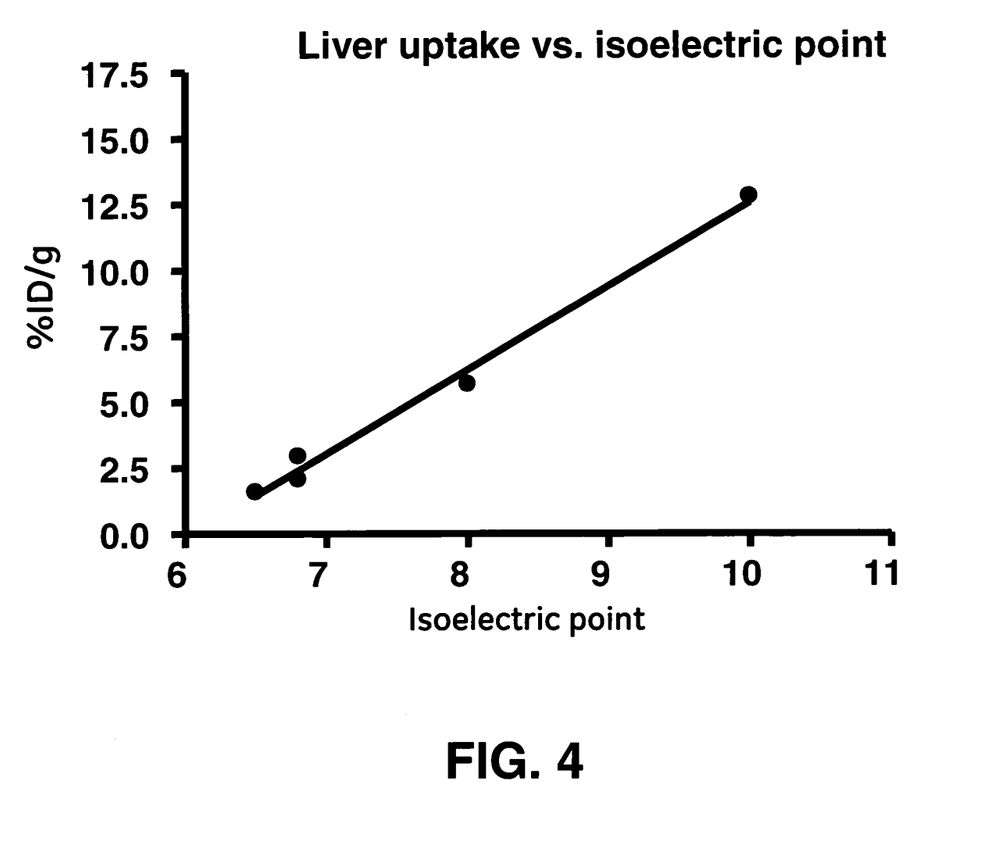
FIG. 4 shows the correlation of liver uptake and isoelectric point. The isoelectric point and observed liver retention at 2 hours post-injection are plotted and fit with a linear regression. The correlation has an r-squared value of greater than 0.98.

The isoelectric points determined from the sequences were plotted against the observed liver retention values at 2 hours post-injection. Correlation was observed between liver and isoelectric point—a correlation that shows that substitutions that do not impact the structure or size of an affibody may be used to control its metabolism by altering its native charge state. In the case of the monomeric affibodies, the slope was significantly non-zero with a p-value of <0.01, and a linear regression r-squared value of 0.983 (FIG. 4).

The Z1978 affibody demonstrated the lowest liver uptake. This low uptake is engineered into the protein via the reduction in isoelectric point. To further reduce uptake, the isoelectric point may be shifted lower using the procedures described above.

The affibody with the highest level of liver retention is Z1995. A comparison of the sequences of Z1995 and Z1978 demonstrates some of the substitutions that can alter (in this case, lower) the isoelectric point of a protein.

The following substitutions in Z1995 will convert it to Z1978:: R20 is mutated to L, L21 is mutated to S, K22 is mutated to D, A25 is mutated to Q, A29 is mutated to S, K36 is mutated to S, S44 is mutated to K, and R47 is mutated to I. In total, the conversion involves a net decrease of 2 basic amino acids, and a net increase of 1 acidic amino acid. Such sequence manipulations (increasing the number of acidic amino acid residues and decreasing the number of basic amino acid residues, or the opposite), are effective at changing the isoelectric point. The isoelectric point may also be changed by substitutions with synthetic basic or acidic amino acids in the context of peptide synthesis or other techniques for producing proteins.

Example 2

A Panel of Dimeric Affibodies

The goal of this study was to apply the invention to multivalent affibodies in order to determine if their in vivo behavior may be manipulated in the same manner as the monovalent affibodies. Multivalent affibodies will have advantages in certain clinical situations and the ability to control their clearance would be valuable.

Two bivalent affibodies, each comprising a single polypeptide chain made up of two identical monovalent affibody sequences with a small intervening linker, were selected for this study. They are referred to by their development names "zTNF" and "zHer2". They were selected from the available dimeric affibodies on the basis of their disparate isoelectric points—9.0 for zHer2 and 5.1 for zTNF.

Both affibodies were conjugated to the hynic chelator via terminal cysteine amino acid residues using maleimide chemistry as discussed above. Conjugation was confirmed by mass spectrometry, and the proteins were intact as evaluated by HPLC. Both affibodies were radiolabeled with 99 mTc as described above. Radiochemical purity was determined to be >95% for both.

Figures 6A, 6B:
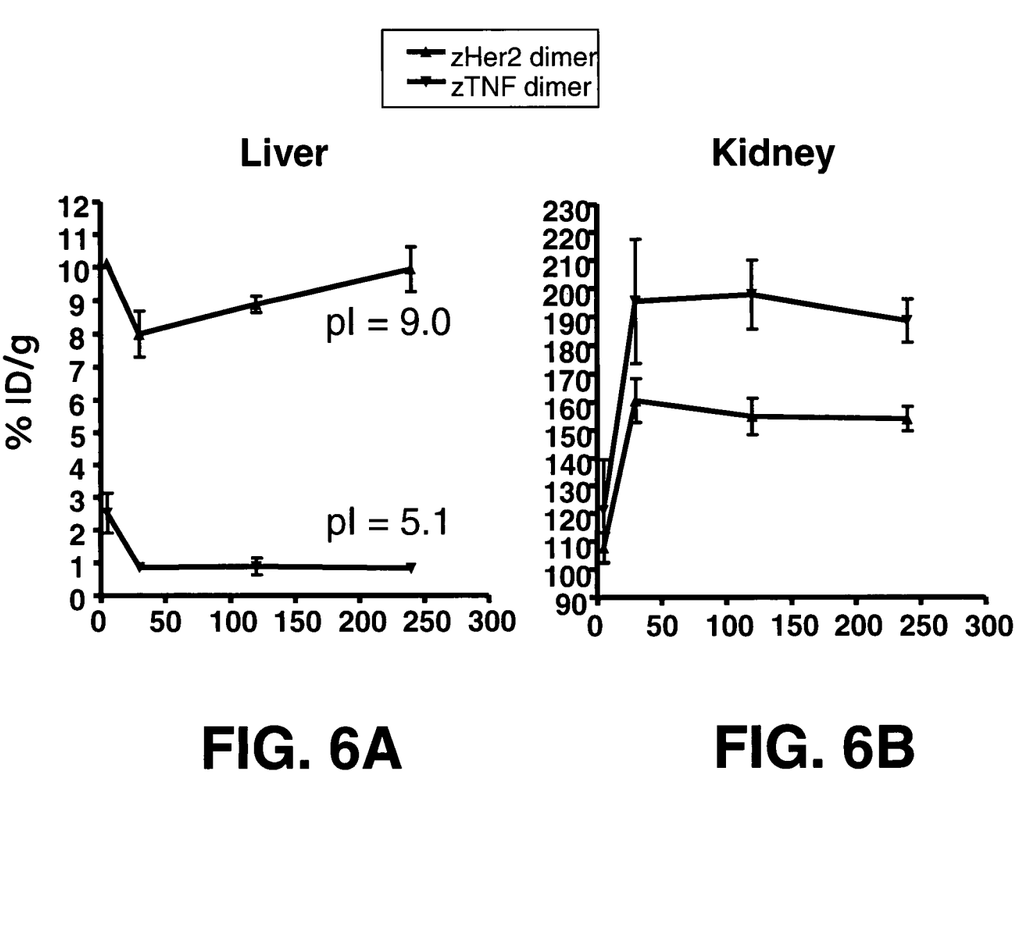

Biodistribution results for both bivalent affibodies were similar to those observed for the monovalent affibodies. Blood clearance curves (FIG. 5) and parameters (table 4) were comparable to the monovalent affibodies. The clearance organs exhibited the same broad range as observed for the monovalent affibodies (FIG. 6).

The primary sequences of the bivalent affibodies (table 2) were used to calculate the isoelectric points as described above. When compared to the liver retention values, the same correlation was observed (FIG. 6). This data shows that the invention may be practiced with multivalent affibodies as well as monovalent ones, and that the effective range of isoelectric points runs at least as low as 5.1.

Example 3

A Panel of Seven Affibodies

The goal of this study was to develop a targeted contrast agent with low non-specific liver retention. In this case, sequences for affibodies with a high affinity for the selected imaging target were analyzed and isoelectric points were determined. The range was observed to be between 6.3 and 8.0.

The affibody with the lowest isoelectric point (called by its development code, "z2465") was chosen for initial experiments. Based on the data discussed above, this molecule should have the lowest non-specific liver retention. The chosen affibody was radiolabeled via its 6-his tag as described above, and biodistribution was carried out. The molecule was cleared with the same parameters as other affibodies, and, as desired, the liver uptake was observed to be low.

Figure 7:
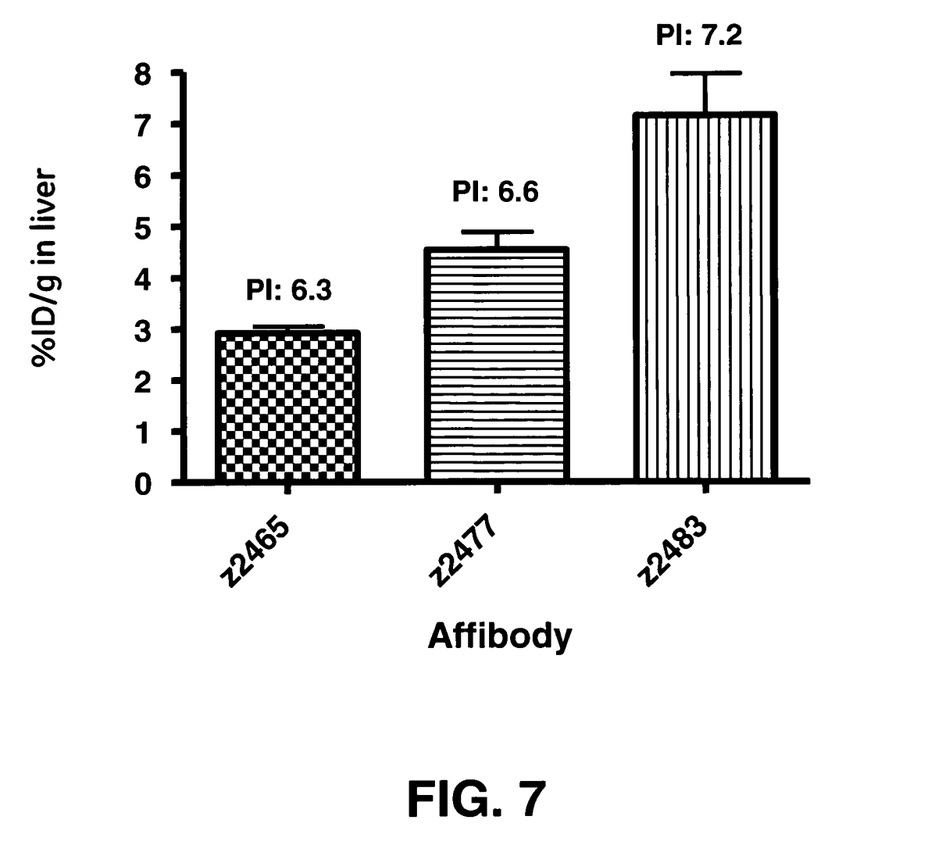
FIG. 7 shows the correlation of liver uptake and isoelectric point. The isoelectric point and observed liver retention at 2 hours post-injection confirm that the use of isoelectric point to direct clearance away from specific organs is effective and can also be used for lead candidate agent selection or down-selection purposes.

To explore and confirm the predictions made based on the current technique, two more affibodies of varying isoelectric point (called by their development codes, "z2477" and "z2483") were chosen from the panel of eight, and a single time-point biodistribution was carried out. According to the examples above, the z2465 affibody chosen for the initial experiment should, by virute of its low isoelectric point, have the lowest liver uptake of the three affibodies analyzed. At two hours post-injection, when the comparisons were made, the correlation between liver retention and isoelectric point was still observed (FIG. 7). This confirmation experiment demonstrated proper function of the invention—the process of using isoelectric point allowed for the rapid selection of the appropriate affibody for development, and will allow for further reduction in liver retention.

The specific substitutions in z2483 that convert it to z2465, and confer upon it lower liver retention are V20 to I and K21 to E. These substitutions result in a net increase of one acidic amino acid residue and a net decrease of one basic amino acid residue—a change that drives the isoelectric point down to 6.3 (from 7.2)

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

We claim:

1. A method of reducing liver or cardiovascular uptake in Vivo in subject in need thereof, of a native polypeptide comprising the amino acid SEQ. ID No. 5 that specifically binds to a PDGF-Rβ of the subject comprising:
   (i) generating a labeled modified polypeptide in vitro by:
      (a) providing the native polypeptide comprising the amino acid sequence of SEQ. ID NO. 5 that specifically binds to the PDGF-Rβ;
      (b) substituting R20, L21, K22, A25, A29, K36, S44, and R47 residues of the native polypeptide from step (a) with L, S, D, Q, S, S, K, and I residues respectively to produce a modified polypeptide comprising the amino acid sequence of SEQ. ID NO. 2, wherein the modified polypeptide (SEQ. ID NO. 2) demonstrates an isoelectric point at least 0.05-0.1 pH points less than the isoelectric point of the native polypeptide;

(c) appending a signal generator to the modified polypeptide to form a labeled modified polypeptide comprising the amino acid sequence of SEQ. ID NO. 2; and (ii) introducing the labeled modified polypeptide of comprising the amino acid sequence of SEQ. ID NO. 2 into the subject to specifically bind to the PDGF-Rβ in vivo.

2. The method of claim 1, wherein the signal generator is selected from radioactive, fluorescent, magnetic, radioopaque, luminescent, phosphorescent, isotopic, or ultrasound opaque signal generator.

3. The method of claim 2, wherein the signal generator comprises 99 mTc or 18 F.

4. The method of claim 1, further comprising a targeting moiety appended to the modified polypeptide.

* * * * *

SEQUENCE LISTING

```
<160> NUMBER OF SEQ ID NOS: 8

<210> SEQ ID NO 1
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gly Ser Ser His His His His His His Leu Gln Val Asp Asn Lys Phe
1               5                   10                  15

Asn Lys Glu Arg Gln Val Ala Ala Ala Glu Ile Asp Ala Leu Pro Asn
            20                  25                  30

Leu Asn Arg Gly Gln Trp Asn Ala Phe Ile Ala Ser Leu Val Asp Asp
        35                  40                  45

Pro Ser Gln Ser Ala Asn Leu Leu Ala Glu Ala Lys Lys Leu Asn Asp
    50                  55                  60

Ala Gln Ala Pro Lys Val Asp
65                  70
```

```
<210> SEQ ID NO 2
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gly Ser Ser His His His His His Leu Gln Val Asp Asn Lys Phe
1               5                   10                  15

Asn Lys Glu Leu Ser Asp Ala Ala Gln Glu Ile Asp Ser Leu Pro Asn
            20                  25                  30

Leu Asn Arg Ser Gln Trp Asn Ala Phe Ile Lys Ser Leu Ile Asp Asp
        35                  40                  45

Pro Ser Gln Ser Ala Asn Leu Leu Ala Glu Ala Lys Lys Leu Asn Asp
    50                  55                  60

Ala Gln Ala Pro Lys Val Asp
65                  70

<210> SEQ ID NO 3
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gly Ser Ser His His His His His Leu Gln Val Asp Asn Lys Phe
1               5                   10                  15

Asn Lys Glu Arg Arg Glu Ala Ala Lys Glu Ile Asp Ser Leu Pro Asn
            20                  25                  30

Leu Asn Arg Thr Gln Trp Asn Ala Phe Ile Arg Ser Leu Ala Asp Asp
        35                  40                  45

Pro Ser Gln Ser Ala Asn Leu Leu Ala Glu Ala Lys Lys Leu Asn Asp
    50                  55                  60

Ala Gln Ala Pro Lys Val Asp
65                  70

<210> SEQ ID NO 4
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Ser Ser His His His His His Leu Gln Val Asp Asn Lys Phe
1               5                   10                  15

Asn Lys Glu Leu Val Arg Ala Ala Gln Glu Ile Asp Glu Leu Pro Asn
            20                  25                  30

Leu Asn Arg Gly Gln Trp Asn Ala Phe Ile Lys Ser Leu Val Asp Asp
        35                  40                  45

Pro Ser Gln Ser Ala Asn Leu Leu Ala Glu Ala Lys Lys Leu Asn Asp
    50                  55                  60

Ala Gln Ala Pro Lys Val Asp
65                  70
```

```
<210> SEQ ID NO 5
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gly Ser Ser His His His His His Leu Gln Val Asp Asn Lys Phe
1               5                   10                  15

Asn Lys Glu Arg Leu Lys Ala Ala Ala Glu Ile Asp Ala Leu Pro Asn
            20                  25                  30

Leu Asn Arg Lys Gln Trp Asn Ala Phe Ile Ser Ser Leu Arg Asp Asp
        35                  40                  45

Pro Ser Gln Ser Ala Asn Leu Leu Ala Glu Ala Lys Lys Leu Asn Asp
65      50                  55                  60

Ala Gln Ala Pro Lys Val Asp
65                  70

<210> SEQ ID NO 6
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gly Ser His His His His His His Leu Gln Val Asp Asn Lys Phe Asn
1               5                   10                  15

Lys Glu Leu Ile Glu Ala Ala Ala Glu Ile Asp Ala Leu Pro Asn Leu
            20                  25                  30

Asn Arg Arg Gln Trp Asn Ala Phe Ile Lys Ser Leu Val Asp Asp Pro
        35                  40                  45

Ser Gln Ser Ala Asn Leu Leu Ala Glu Ala Lys Lys Leu Asn Asp Ala
    50                  55                  60

Gln Ala Pro Lys Val Asp Cys
65                  70

<210> SEQ ID NO 7
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Ser His His His His His His Leu Gln Val Asp Asn Lys Phe Asn
1               5                   10                  15

Lys Glu Leu Ile Ala Ala Ala Ala Glu Ile Asp Arg Leu Pro Asn Leu
            20                  25                  30

Asn Arg Val Gln Trp Asn Ala Phe Ile Lys Ser Leu Val Asp Asp Pro
        35                  40                  45

Ser Gln Ser Ala Asn Leu Leu Ala Glu Ala Lys Lys Leu Asn Asp Ala
    50                  55                  60

Gln Ala Pro Lys Val Asp Cys
65                  70

<210> SEQ ID NO 8
```

```
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gly Ser His His His His His Leu Gln Val Asp Asn Lys Phe Asn
1               5                   10                  15

Lys Glu Leu Val Lys Ala Ala Ala Glu Ile Asp Ala Leu Pro Asn Leu
            20                  25                  30

Asn Arg Arg Gln Trp Asn Ala Phe Ile Lys Ser Leu Val Asp Asp Pro
        35                  40                  45

Ser Gln Ser Ala Asn Leu Leu Ala Glu Ala Lys Lys Leu Asn Asp Ala
    50                  55                  60

Gln Ala Pro Lys Val Asp Cys
65                  70
```